US006676707B2

(12) United States Patent  (10) Patent No.: US 6,676,707 B2
Yih et al.  (45) Date of Patent: Jan. 13, 2004

(54) PROSTHETIC DEVICES FOR UPPER AND LOWER LIMBS

(76) Inventors: Tachung C. Yih, 1329 Lyra La., Arlington, TX (US) 76013; Sankar Pemmaraju, 6141 Avery Dr., #7210 Ft. Worth, TX (US) 76132

(*) Notice: Subject to any disclaimer, the term of this patent is extended or adjusted under 35 U.S.C. 154(b) by 21 days.

(21) Appl. No.: 09/864,504

(22) Filed: May 24, 2001

(65) Prior Publication Data

US 2002/0177905 A1 Nov. 28, 2002

(51) Int. Cl.[7] .............................. A61F 2/64; A61F 2/68
(52) U.S. Cl. ............................ 623/24; 623/26; 623/39; 623/43
(58) Field of Search ...................... 623/39, 43, 44, 623/24, 26; A61F 2/64

(56) References Cited

U.S. PATENT DOCUMENTS

| | | | | |
|---|---|---|---|---|
| 3,806,958 A | * | 4/1974 | Gusev ........................ | 623/39 |
| 4,690,327 A | | 9/1987 | Takai et al. | |
| 4,961,416 A | * | 10/1990 | Moore et al. ................ | 623/39 |
| 5,020,790 A | * | 6/1991 | Beard et al. ................. | 623/24 |
| 5,201,776 A | * | 4/1993 | Freeman ...................... | 623/46 |
| 5,314,498 A | * | 5/1994 | Gramnas ...................... | 623/39 |
| 5,545,232 A | * | 8/1996 | Van de Veen ................. | 623/39 |
| 5,728,173 A | * | 3/1998 | Chen .......................... | 623/44 |
| 5,904,721 A | * | 5/1999 | Henry et al. ................. | 623/26 |
| 6,314,828 B1 | | 11/2001 | Yih | |
| 6,423,098 B1 | * | 7/2002 | Biedermann ................. | 623/24 |

* cited by examiner

Primary Examiner—David H. Willse
Assistant Examiner—Javier G. Blanco
(74) Attorney, Agent, or Firm—Arthur F. Zobal; Geoffrey A. Mantooth

(57) ABSTRACT

The invention is directed to a prosthesis which includes first and second members pivotally coupled together and two links which are pivotally coupled together with one link being pivotally coupled to the first member and the other link being pivotally coupled the second member. A control mechanism is provided which is pivotally coupled to the first member and the pivotal connection of the two links to move the two links and hence the second member relative to the first member. The first member may be coupled to a person to allow the prosthesis to serve in one embodiment as an arm or as a portion of an arm and in another embodiment to serve as a leg or as a portion of a leg.

22 Claims, 21 Drawing Sheets

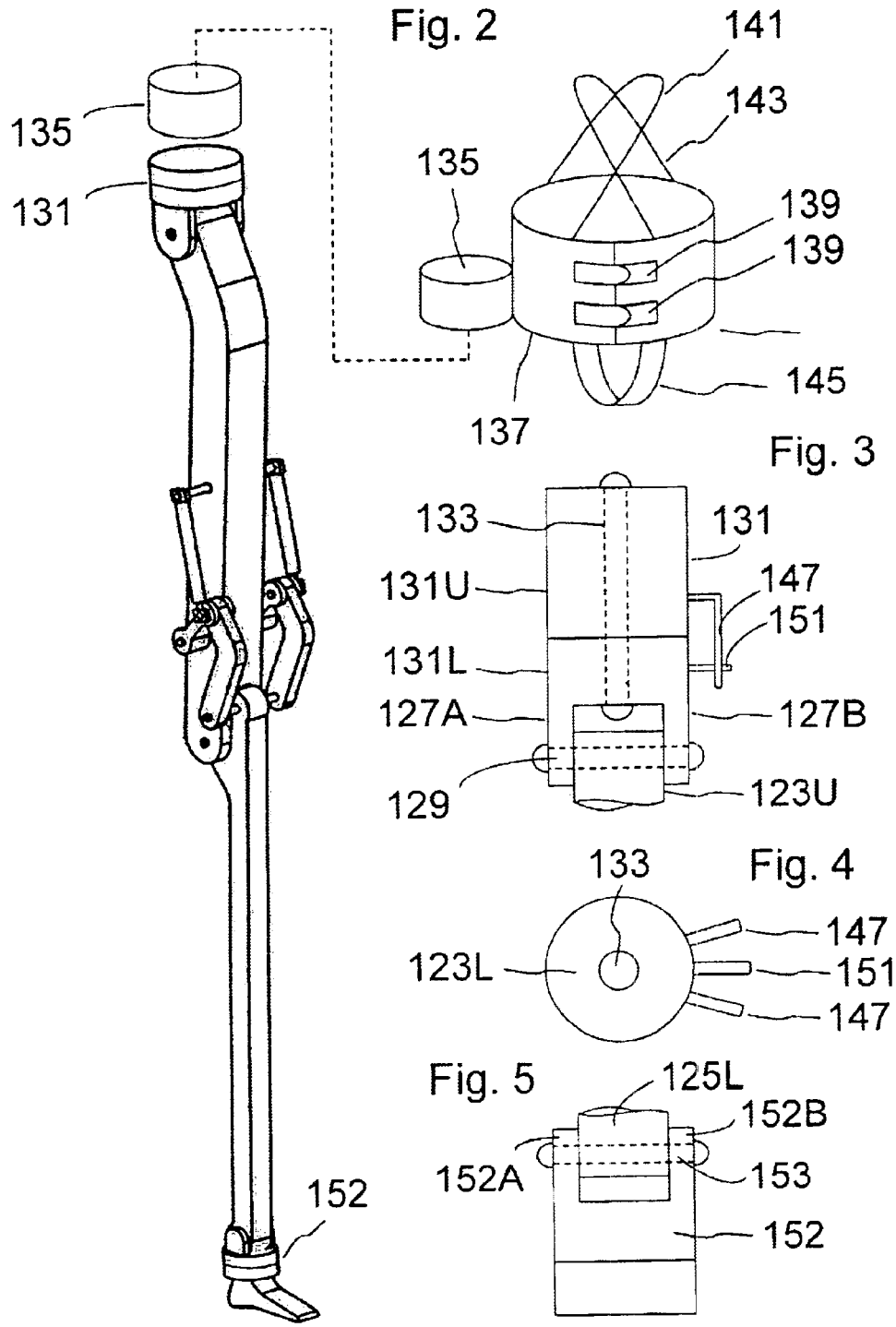

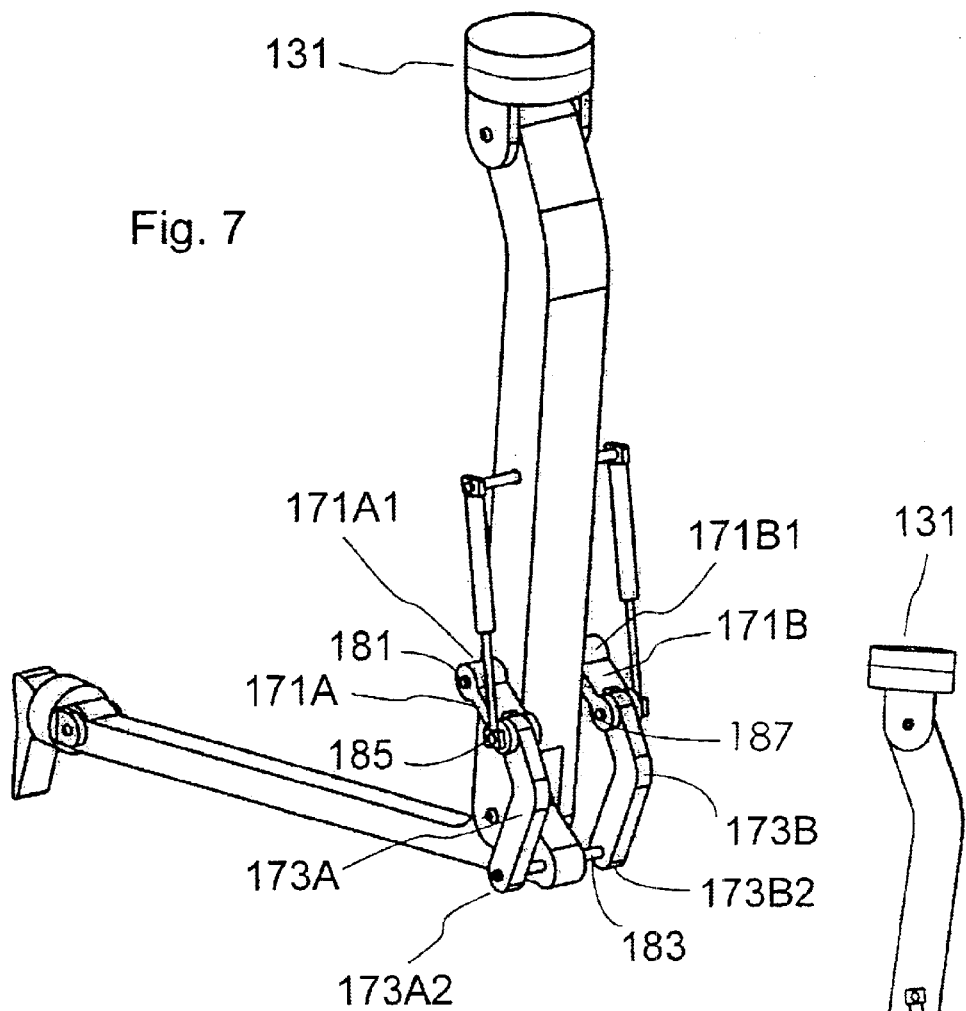

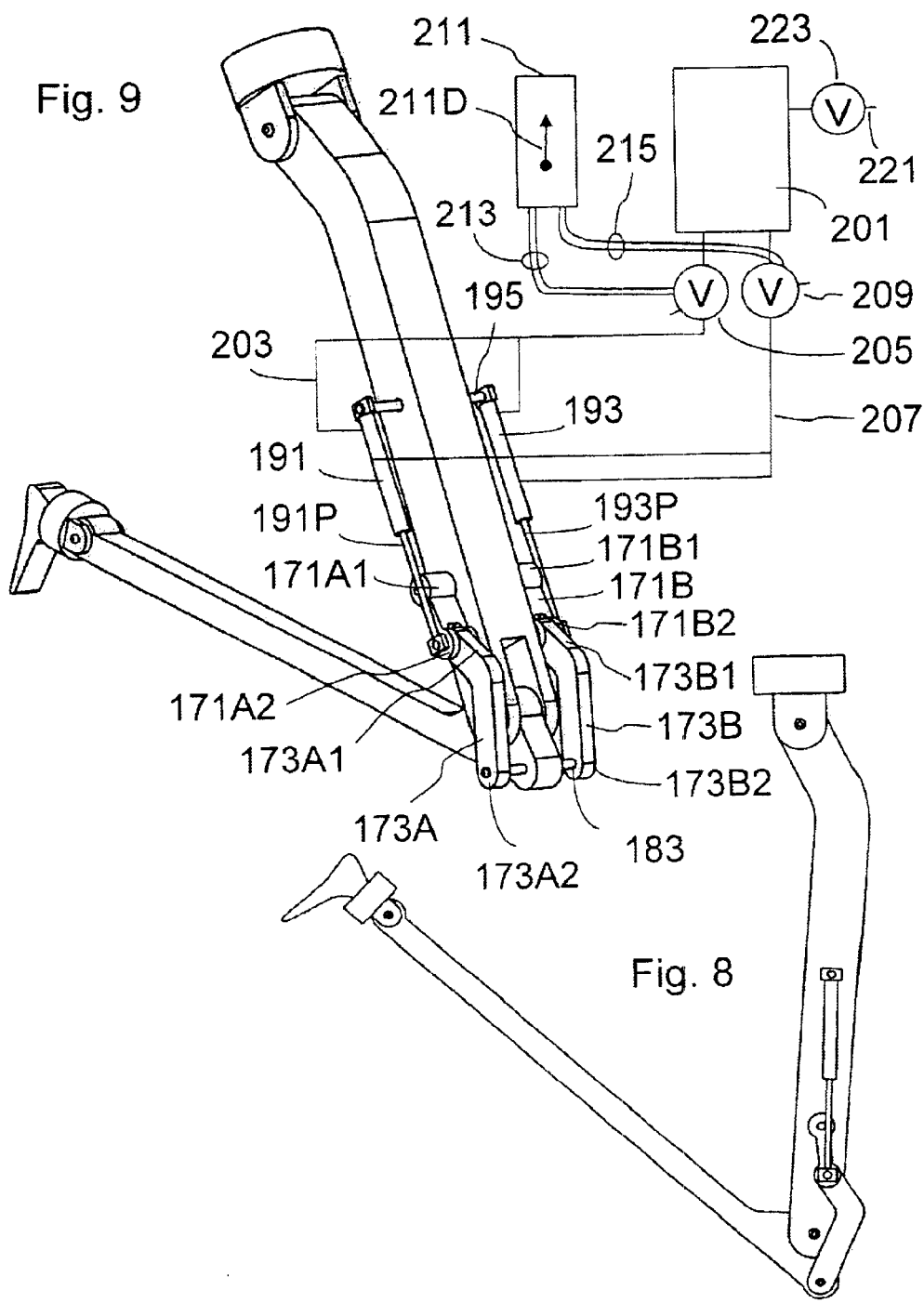

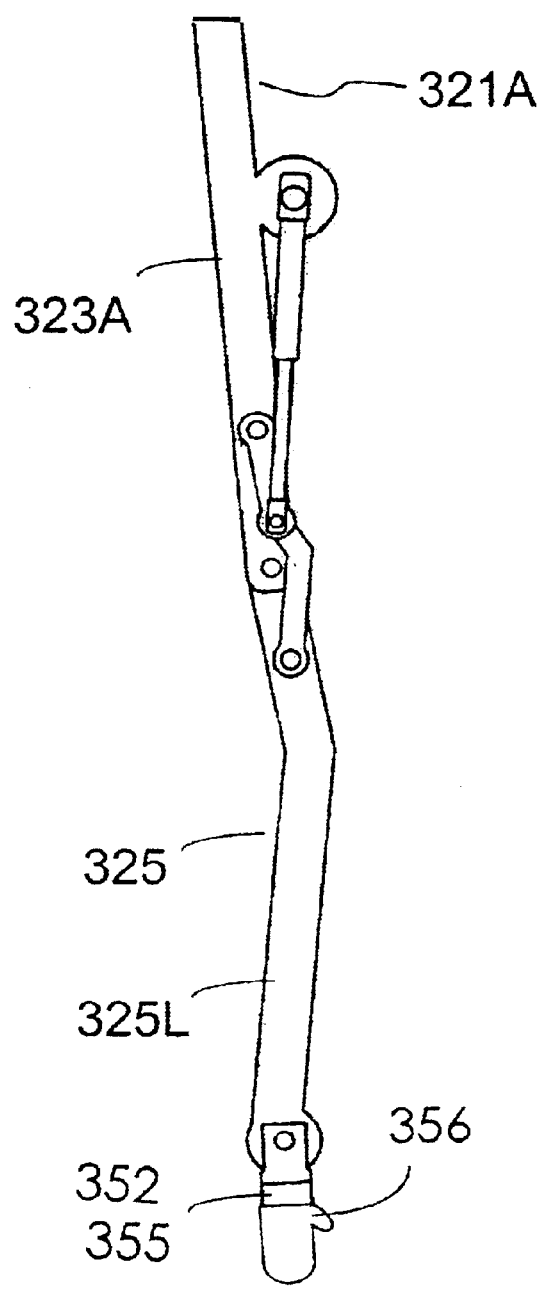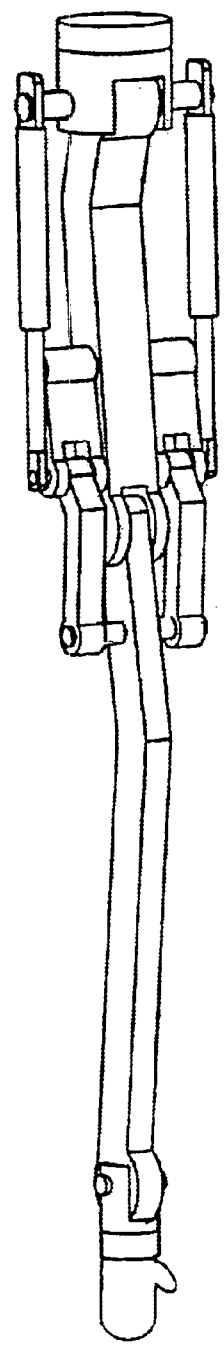

PROSTHETIC DEVICES FOR UPPER AND LOWER LIMBS

BACKGROUND OF THE INVENTION

1. Field of the Invention

The invention relates to prosthetic devices which can serve as arms and legs for people.

2. Summary of the Invention

The invention is directed to a prosthesis which comprises first and second members pivotally coupled together and two links which are pivotally coupled together with one link being pivotally coupled to the first member and the other link being pivotally coupled to the second member. Control means is provided which is pivotally coupled to the first member and to the pivotal connection of the two links to move the two links and hence the second member relative to the first member. The first member may be coupled to a person to allow the prosthesis in one embodiment to serve as an arm and in another embodiment to serve as a leg of a person.

In another embodiment, the first member may be coupled to the upper portion on an arm to allow the prosthesis to serve as the lower portion of the arm. In still another embodiment, the first member may be coupled to the upper portion of a leg to allow the prosthesis to serve as the lower portion of the leg.

BRIEF DESCRIPTION OF THE DRAWINGS

FIG. 2 is an isometric view of the prosthesis of FIG. 1 showing a strap for securing the prosthesis to the waist of a person.

FIG. 3 illustrates a device for rotating the lower portion of the prosthesis relative to the upper portion.

FIG. 4 is a top view of the device of FIG. 3.

FIG. 5 illustrates an apparatus for rotating the lower foot relative to the lower portion of the prosthesis.

FIG. 6 is a side view of the prosthesis of FIG. 1 showing the lower portion rotated about 90 degrees relative the upper portion.

FIG. 7 is an isometric view of the prosthesis of FIG. 6.

FIG. 8 is a side view of the prosthesis of FIG. 1 showing the lower portion rotated to an acute angle relative to the upper portion.

FIG. 9 is an isometric view of the prosthesis of FIG. 8 illustrating a system for actuating the pistons of the cylinders coupled to the device.

FIG. 28 is a side view of a prosthesis of the invention which serves as a replacement of a portion of a person's arm wherein the arm between the shoulder and the elbow has been amputated.

FIG. 29 is an isometric view of the prosthesis of FIG. 28.

DESCRIPTION OF THE PREFERRED EMBODIMENT

Figure 1:
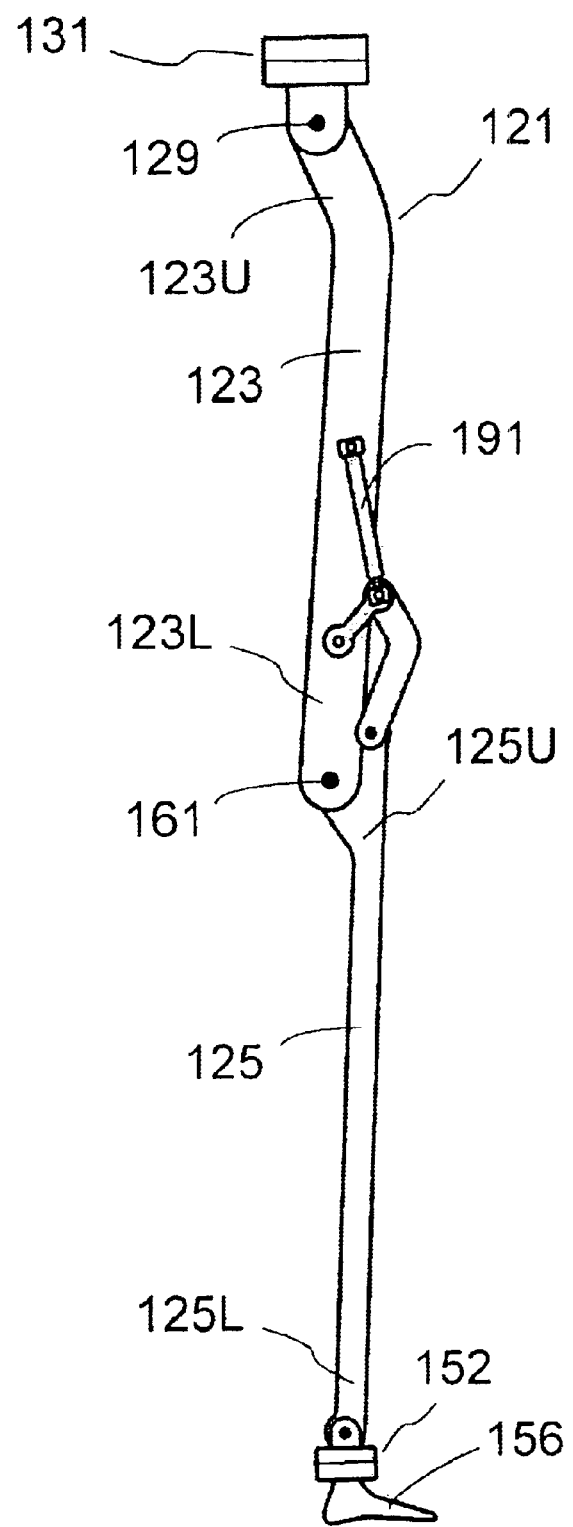
FIG. 1 is a side view of a prosthesis of the invention which can serve as a total replacement of a person's leg.
Figure 10:
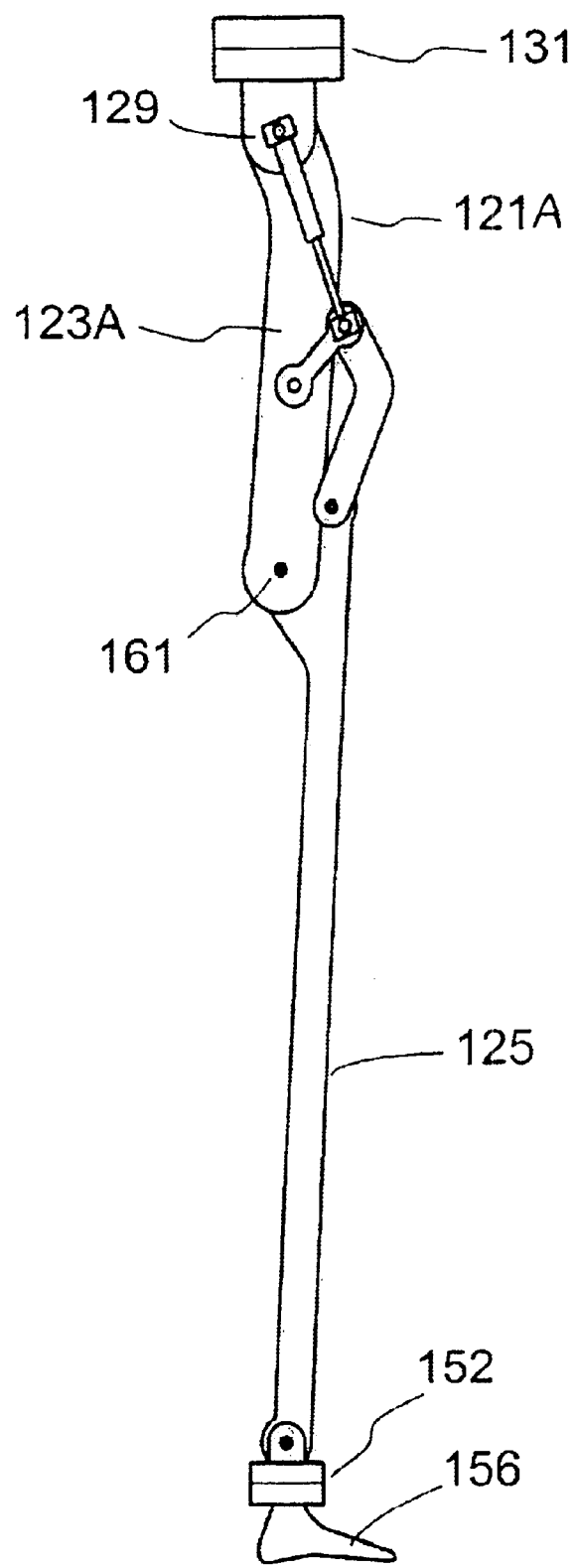
FIG. 10 is a side view of a prosthesis of the invention which serves as a replacement of a portion of a person's leg wherein a portion of the thigh has been amputated.
Figure 11:
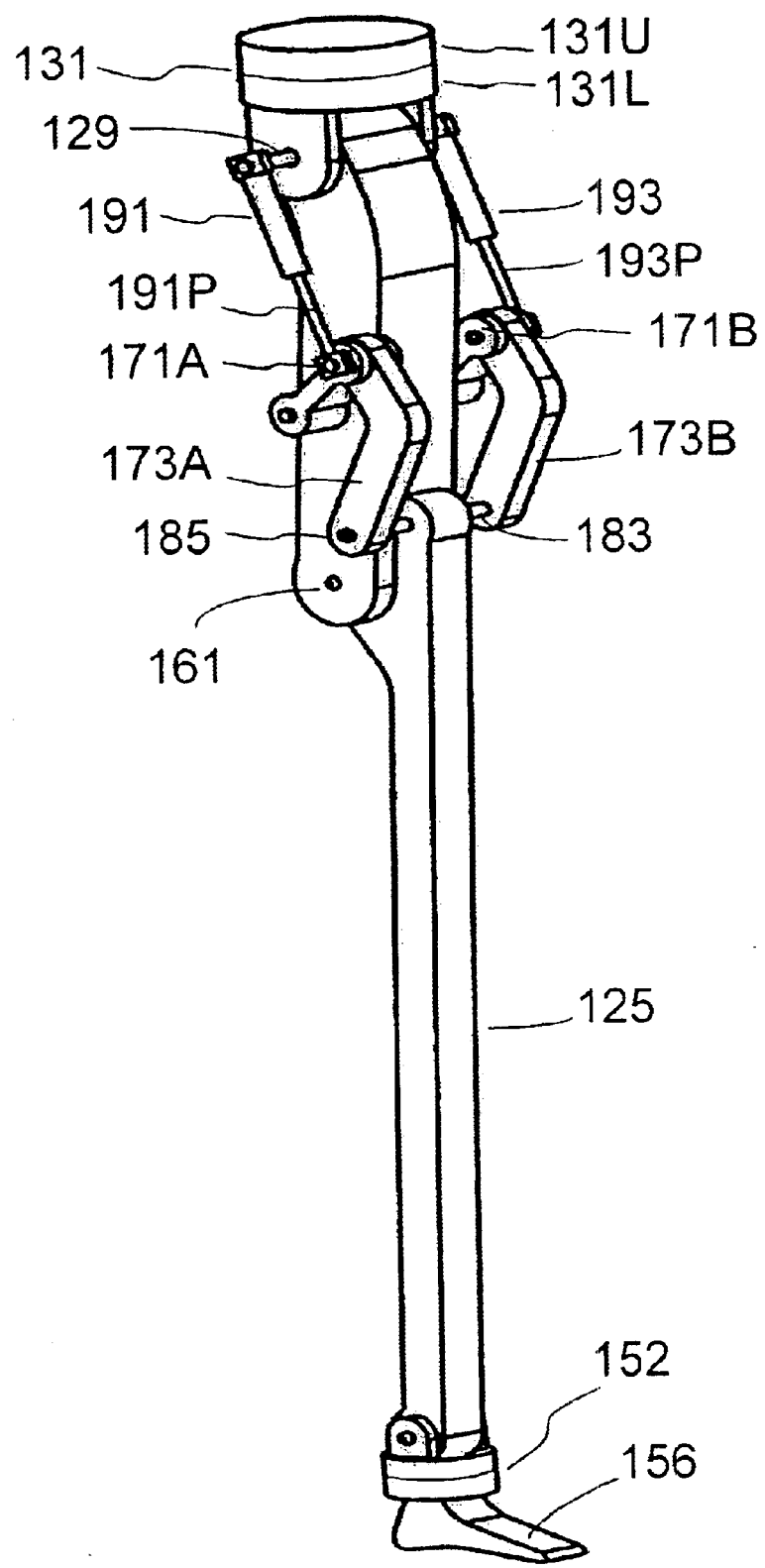
FIG. 11 is an isometric view of the prosthesis of FIG. 10 showing a socket for connecting the upper portion of the prosthesis to a person's thigh and a system for rotating the lower portion of the prosthesis relative to the upper portion.

Referring now to FIGS. 1–9 of the drawings, there will be described a prosthesis 121 which may be used as a total leg replacement. The device 121 comprises a first or upper portion 123 having an upper end 123U and a lower end 123L and a second or lower portion 125 having an upper portion 125U and a lower end 125L. The upper end 123U is pivotally coupled to two plates 127A and 127B by a pin 129 which in turn are connected to a connecting portion 131L of an upper connecting member 131 comprising the lower portion 131 L which is rotatably coupled to an upper portion 131U by a pin 133. Bearings(not shown) may be located between the members 131U and 131L the upper portion 131U can be fixedly located in a socket 135 secured to a flexible belt 137 by screws (not shown) which belt is adapted to fit around a person's waist secured thereto by VELCRO® belts 139, or by belts that have buckles and tongues(not shown), and flexible straps 141, 143, 145. The straps 141, 143 may be coupled around a person's shoulder-neck on each side and the strap 145 may extend around the person's crotch. Although not shown, the straps 141, 143, 145 may have tightening means such as buckles.

Two spaced apart L shaped rods 147 are connected to the member 131U and extend downward. An exterior pin 151 is connected to member 131L and extends outward between rods 147 to limit rotational movement of member 131L relative to member 131U.

The lower end 125L of member 125 is pivotally coupled to the plates 152A and 152B of member 152 by way of a pin 153. The foot 156, fixed to member 152, rotates about pin 153 only.

The lower end 123L of member 123 is pivotably coupled to the upper end 125U of member 125 by a pin 161.

Two pairs of links 171A, 171B and 173A, 173B are pivotably coupled to member 123 and member 125 respectively and to each other for causing rotational or pivotal movement of member 125 relative to member 123 when actuated by a cylinder and piston arrangement. Links 171A and 171B have ends 171A1 and 171B1 pivotably coupled to the member 123 by a pin 181. Links 173A and 173B have ends 173A2 and 173B2 pivotably coupled to an upper end portion of member 125 by a pin 183. The ends 171A2 and 171B2 of links 171A and 171B are pivotably coupled to the ends 173A1 and 173B1 by pins 185 and 187.

Two linear actuators (e.g. pneumatic or hydraulic cylinder) 191 and 193 have ends pivotably coupled to member 123 at a position between its two ends 123U and 123L by a pin 195. Assume that the pneumatic cylinders are use. The cylinders 191 and 193 have pistons 191P and 193P with their ends pivotably coupled to the pins 185 and 187 respectively of the connections between links 171A and 173A and between links 171B and 173B respectively.

A portable container 201 for containing air under pressure has a flexible tube 203 with a valve 205 coupled to cylinders 191 and 193 on one side of the heads of the pistons 191P and 193P and a flexible tube 207 with a valve 209 coupled to cylinders 191 and 193 on the other side of the heads of the pistons 191P and 193P. The valves 205 and 209 may be three way electrically controlled valves. A control system 211 has electrical leads 213 and 215 coupled to the valves 205 and 209 for opening one valve and closing and venting the other valve for retracting the pistons 191P and 193P or extending the pistons 191P and 193P for moving the member 125 relative to member 123. Control of the unit 211 is carried out by movement of a dial 211D.

The units 201 and 211 may be carried by the person or carried by a wheeled cart of the like moved by the person. The container 201 may be re-pressurized by way of line 221 having a one way valve 223.

In using the member 121, it will be attached to a person without a leg in a position to serve as the missing leg as discussed above using the belt 137, straps 141, 143, 145, and the socket 135. The person may use the good leg for most of the walking effort and swing the prosthesis 121 about the pin 129 which has limited rotation about pin 133 to aid in the walking effort. Pivotal movement of the foot 156 with limited rotational movement about pin 153 also aids in the walking movement. The user may carry the source 201 and control 211 as mentioned above and with learned effort should be able to pivot or rotate the two members 123 and 125 about the pin 161 by properly moving the dial 211D, also to aid in the walking effort. When sitting down, the user can move the dial 211D to pivot the member 125 to positions shown in FIGS. 6–9 to move the member 125 to a comfortable position. When standing up, the user can use to dial 211D to straighten and move the members 123 and 125 to a more comfortable walking position.

The socket 135 and strap 137, 141, 143, 145 are shown only in FIG. 2, however, it is to be understood that they will be employed in the prosthesis shown in all of FIGS. 1–9. The source 201, valves, and conduits and the control system 211 and its leads are shown only in FIG. 9, however, it is to be understood that they will be employed in the prosthesis shown in all of FIGS. 1–9. The control unit 211 may have a battery to control the valves 205 and 209. In the embodiment of FIGS. 1–9, the members 123, 125, 171A, 173A, 171B, 173B, 131, 127A, 127B, 152, 156 and other components may be formed of a suitable material such as stainless steel or aluminum.

Figure 12:
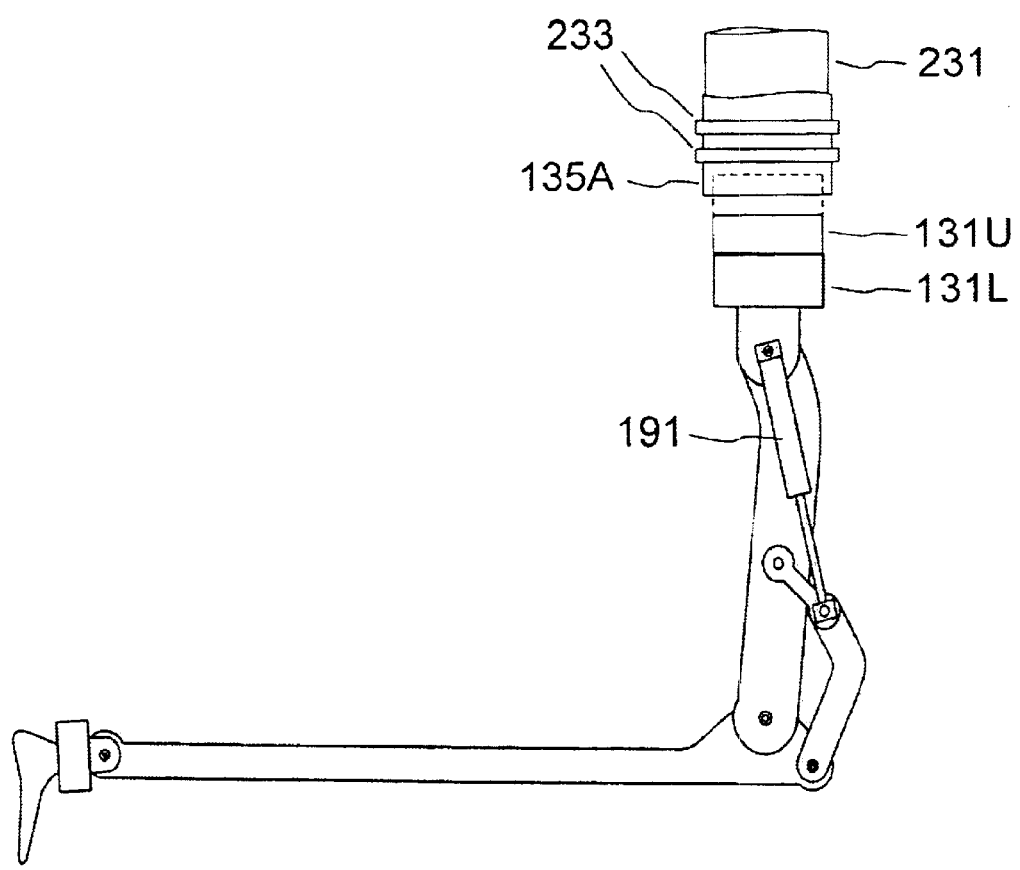
FIG. 12 is a side view of the prosthesis of FIGS. 10 and 11 with the lower portion rotated about 90 degrees relative to the upper portion and also a device for connecting the prosthesis to the thigh of a person.
Figure 13:
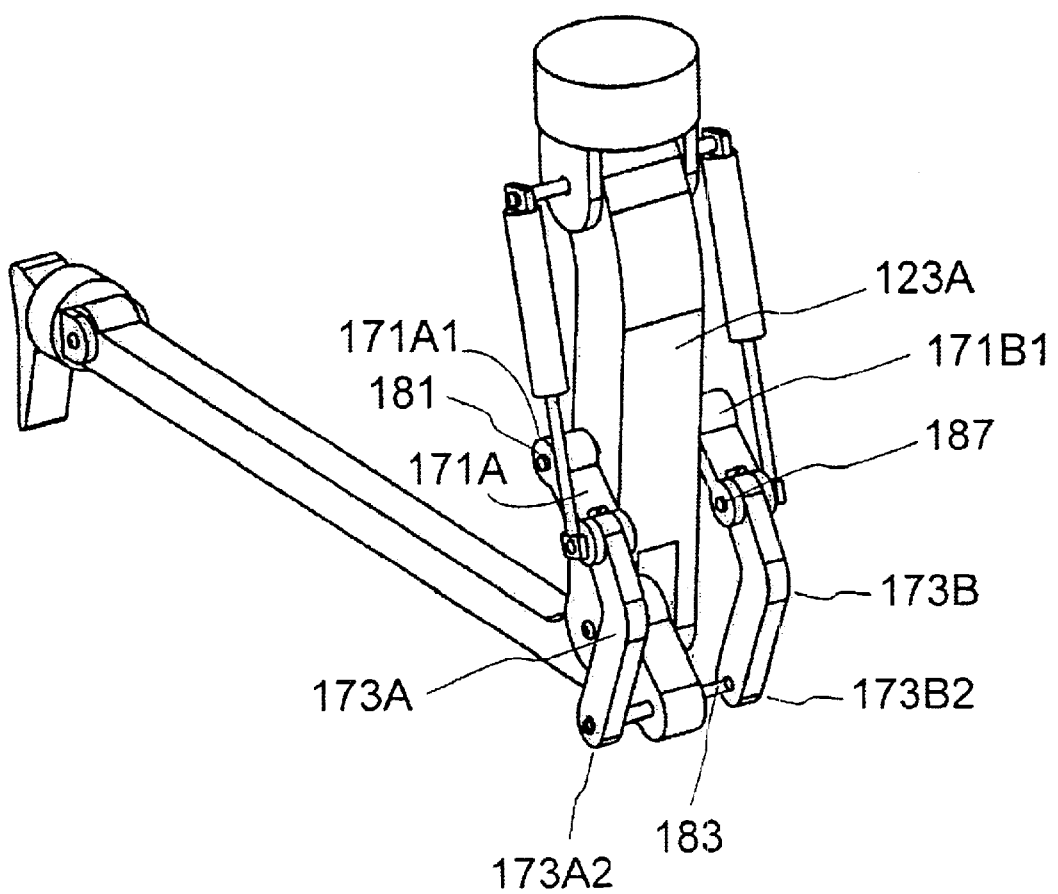
FIG. 13 is an isometric view of the prosthesis of FIG. 12.
Figure 14:
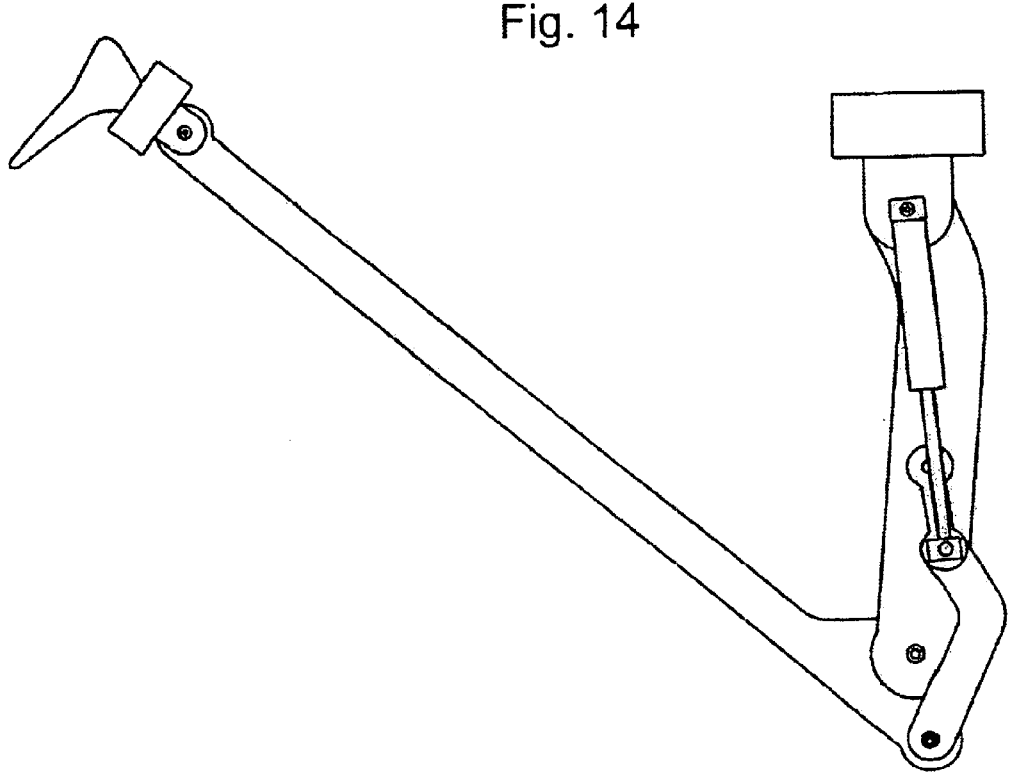
FIG. 14 is a side view of the prosthesis of FIG. 10 with the lower portion rotated to a position which forms an acute angle relative to the upper portion.
Figure 15:
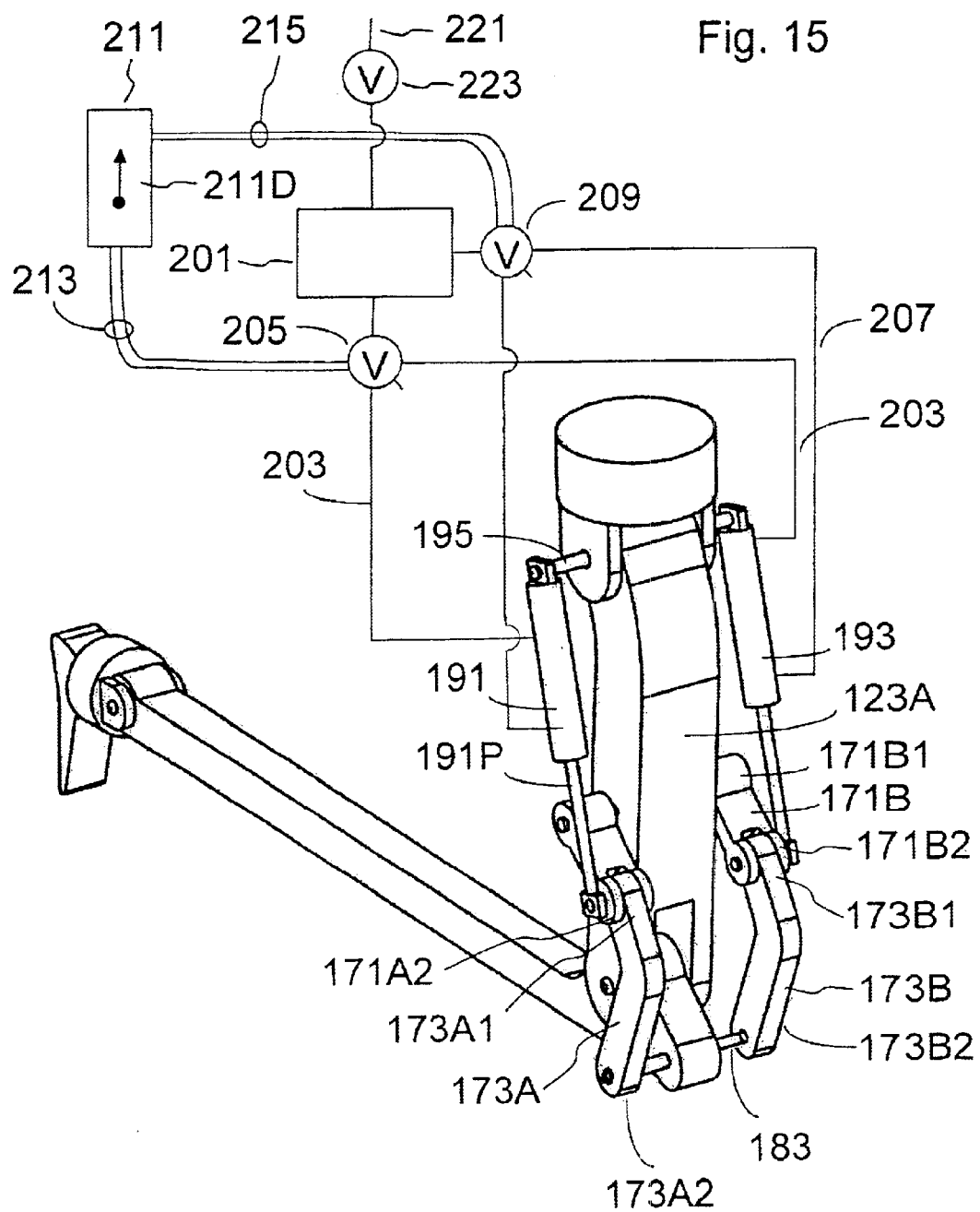
FIG. 15 is an isometric view of the prosthesis of FIG. 14 and a system for actuating the pistons of the cylinders coupled to the device.
Figure 16:
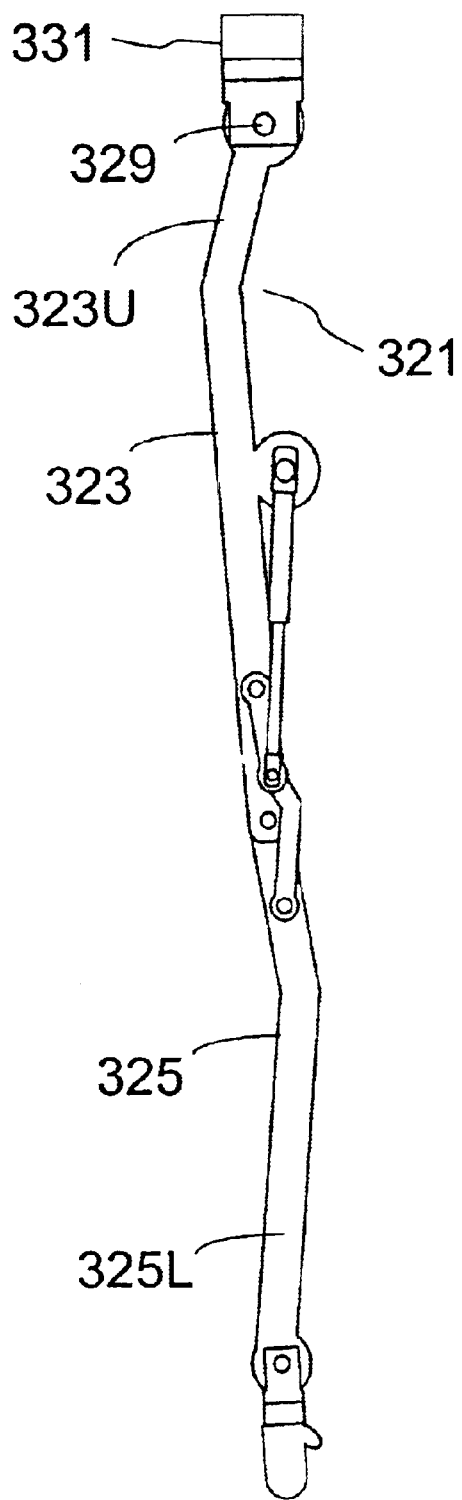
FIG. 16 is a side view of a prosthesis of the invention which can serve as a total replacement of a person's arm.
Figure 17:
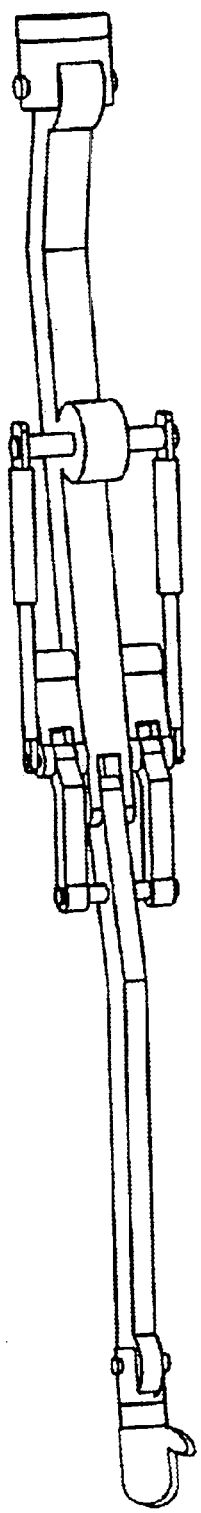
FIG. 17 is an isometric view of the prosthesis of FIG. 16.
Figure 18:
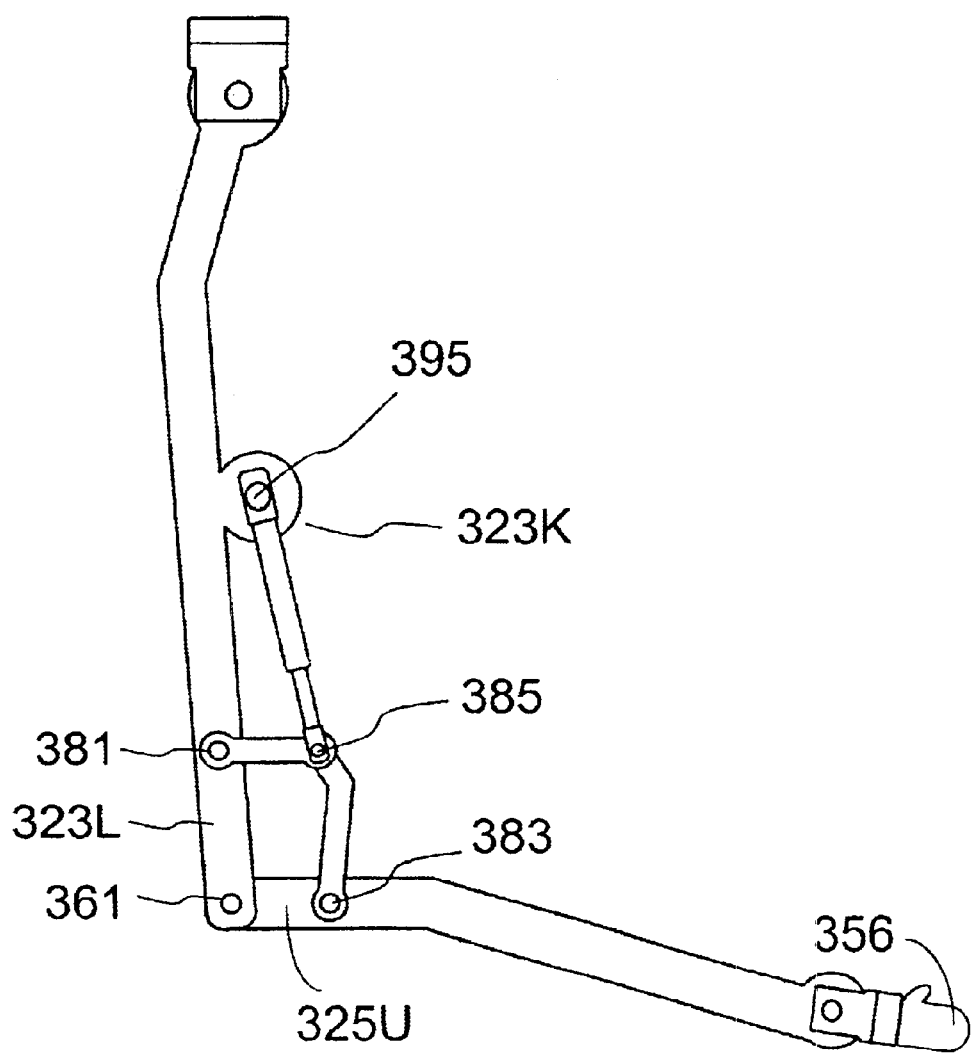
FIG. 18 is a side view of the prosthesis of FIG. 16 with the lower portion rotated to a position of about 90 degrees relative to the upper portion.
Figure 19:
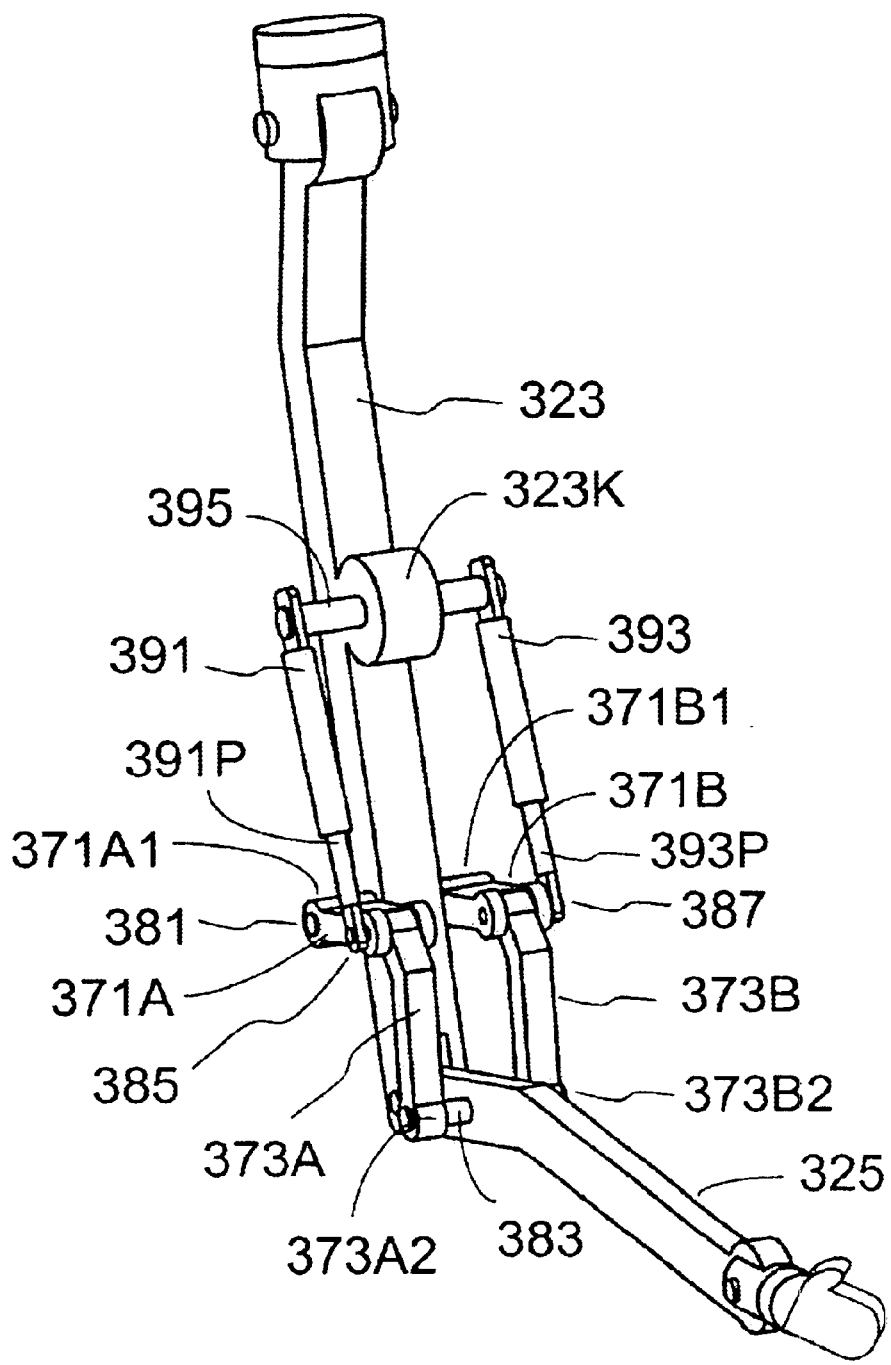
FIG. 19 is an isometric view of the prosthesis of FIG. 16.
Figures 20, 21:
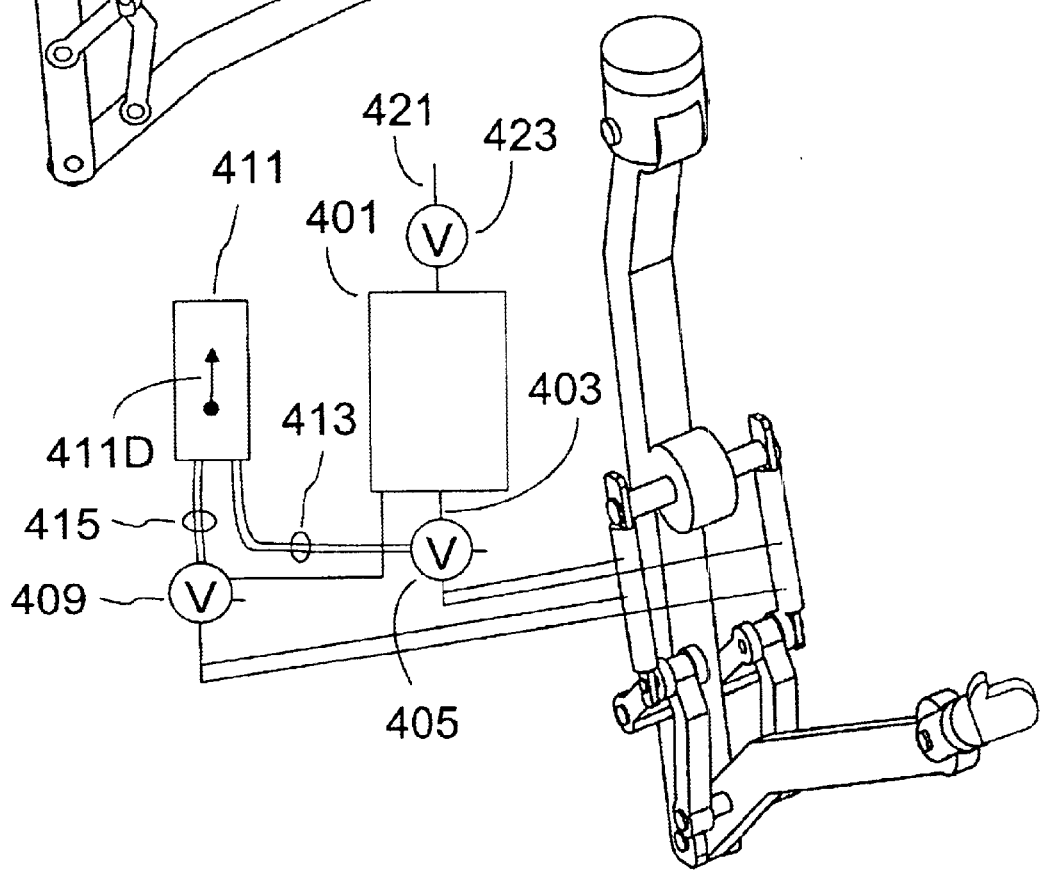
FIG. 20 is a side view of the prosthesis of FIG. 16 with the lower portion rotated to a position which forms an acute angle relative to the upper portion.
FIG. 21 is an isometric view of the prosthesis of FIG. 20 with a system for actuating the pistons of the cylinders coupled to the device.
Figure 22:
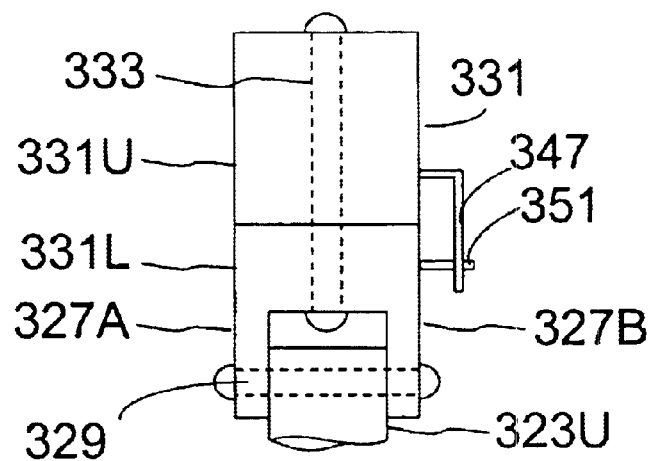
FIG. 22 is an apparatus for rotating the prosthesis relative to its upper connecting portion.
Figure 23:
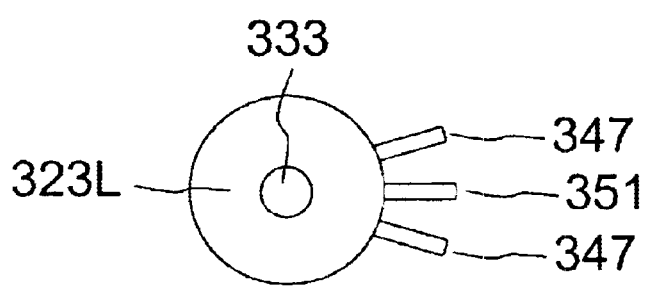
FIG. 23 is a top plan view of FIG. 22.

Referring now to FIGS. 10–15 the prosthetic device 121A is the same as that of FIGS. 1–9 except that the member 123A is shorter than member 123 and the cylinders 191 and 193 are pivotably coupled to pivot pin 129. The device 121A will be used to replace a lower leg where the upper leg has been amputated between the hip and the knee. In FIGS. 10–15 like components are the same as those in FIGS. 1–9. The device 121A also comprises members 125, 131U, 131L, 152, 156, cylinders 191, 193 and pistons 191P and 193P which are the same as those of FIGS. 1–9; source 201, control unit 211, valves 205, 209 which are the same as those of FIGS. 1–9 all of which operate the same as the corresponding members of FIGS. 1–9. In this respect by controlling unit 211 to control the cylinders-pistons 191, 191P and 193, 193P, the lower member 125 can be moved to the positions shown in FIGS. 10–15. The socket 135 will not be employed. Instead, a longer and larger diameter socket 135A will be used. It will be secured to the member 131U and the amputated thigh 231 will be inserted into the other end of the socket 135A and secured in place by straps 233 as shown in FIG. 12.

The members 131U and 131L will have the rotational limitation stops 147 and 151 as shown in FIGS. 2–5.

Referring now to FIGS. 16–27, there will be described a prosthesis 321 for use as a total arm replacement. The device 321 comprises a first of upper portion 323 having an upper end 323U and a lower end 323L and a second or lower portion 325 having an upper portion 325U and a lower end 325L. The upper end 323U is pivotally coupled to two plates 327A and 327B by a pin 329 which in turn are connected to a connecting portion 331L of an upper connecting member 331 comprising the lower portion 331L which is rotatably coupled to an upper portion 331U by a pin 333. Bearings(not shown) may be located between the members 331U and 331L.

Figure 24:
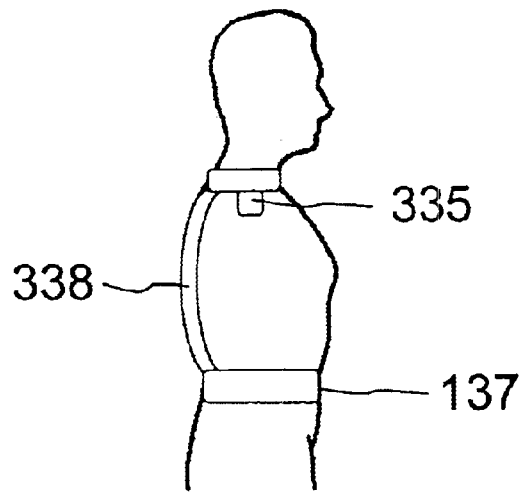
FIG. 24 illustrates a system for strapping the prosthesis of FIG. 16 to a person.
Figure 25:
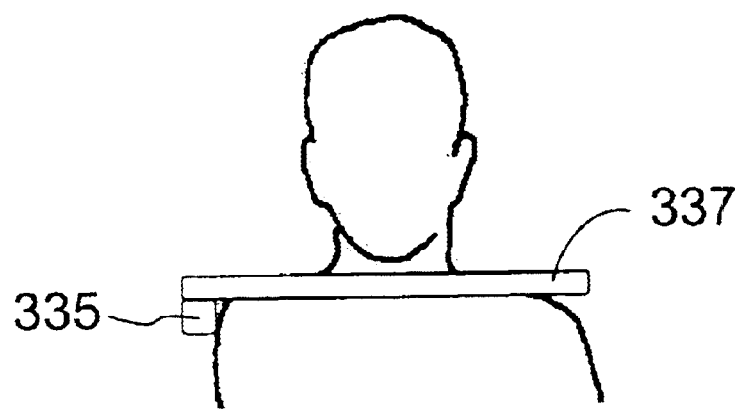
FIG. 25 is a front view of the system of FIG. 24.

The upper portion 331U can be fixedly located in a socket 335 secured to a shoulder pad device 337 having a connecting member 338 extending from the pad 337 down to the strap 137 as shown in FIGS. 24 and 25. The strap 137 is the same as strap 137 of FIG. 2 except the socket 135 is not used.

Two spaced apart L shaped rods 347 are connected to the member 331U and extend downward. An exterior pin 351 is connected to member 331L and extends outward between rods 347 to limit rotational movement of member 331L relative to member 331U.

The lower end 325L of member 325 is pivotally coupled to the plates 352A and 352B of member 352 by way of a pin 353. Rotatably coupled to the lower end of member 352 by way of a pin 354 is a member 355 which is connected to a hand type device 356. The member 352 has two spaced apart L shaped rods 347 coupled thereto and member 354 has an exterior pin 351 which extends outward between rods 347 to limit rotational movement of the hand member 355 relative to member 352.

The lower end 323L of member 323 is pivotally coupled to the upper end 325U of member 325 by a pin 361.

Two pairs of links 371A, 371B and 373A, 373B are pivotally coupled to a knob 323K of member 323 and member 325 respectively and to each other for causing pivotal or rotational movement of member 325 relative to member 323 when actuated by a cylinder and piston arrangement. Links 371A and 371B have ends 371A1 and 371B1 pivotally coupled to the member 321 by a pin 381. Links 373A and 373B have ends 373A2 and 373B2 pivotally coupled to an upper end portion of member 325 by a pin 383. The ends 371A2 and 371B2 of links 371A and 371B are pivotally coupled to the ends 373A1 and 373B1 respectfully by pins 385 and 387.

Two pneumatic cylinders 391 and 393 have ends pivotally coupled to member 323 at a position between its two ends 323U and 323L by a pin 395. The cylinders 391 and 393 have pistons 391P and 393P with their ends pivotally coupled to the pins 385 and 387 respectively of the connections between links 371A and 373A and between links 371B and 373B respectively.

A portable container 401 for containing air under pressure has a flexible tube 403 with a valve 405 coupled to cylinders 391 and 393 on one side of the heads of pistons 391P and 393P and a flexible tube 407 with a valve 409 coupled to cylinders 391 and 393 on the other side of the heads of the pistons 391P and 393P. The valves 405 and 409 may be three way electrically controlled valves. A control system 411 has electrical leads 413 and 415 coupled to the valves 405 and 409 for opening one valve and closing and venting the other valve for retracting the pistons 391P and 393P or for extending the pistons 391P and 393P for moving the member 325 relative to member 323. Control of the unit 411 is carried out by movement of a dial 411D.

The members 401 and 411 may be carried by the person or carried by a wheeled cart of the like moved by the person. The container 401 may be re-pressurized by way of line 421 having a one way valve 423.

In using the member 321, it will be attached to a person without an arm in a position to serve as the missing arm as discussed above using the socket 335 and straps 137, 337 and 338. The person may swing the prosthesis about the pin 329 which has limited rotation about pin 333. The user may carry the source 401 and control 411 as mentioned above and with learned effort should be able to pivot the two members 323 and 325 about the pin 361 by properly moving the dial 411D.

The socket 335 and straps 137, and 337, 338 are shown only in FIGS. 24 and 25, however it is to be understood that they will be employed in the prosthesis shown in all of FIGS. 16–27. The source 401 and valves and conduits and the control system 411 and its leads are shown only in FIG. 21, however, it is to be understood that they will be employed in the prosthesis shown in all of FIGS. 16–27. The control unit 411 may have a battery to control the valves 405 and 409. In the embodiment of FIGS. 16–27, the members 323, 325, 371A, 373A, 371B, 373B, 331, 327A, 327B, 352, 355, 356 and other components may be formed of a suitable material such a stainless steel or aluminum.

Figure 33:
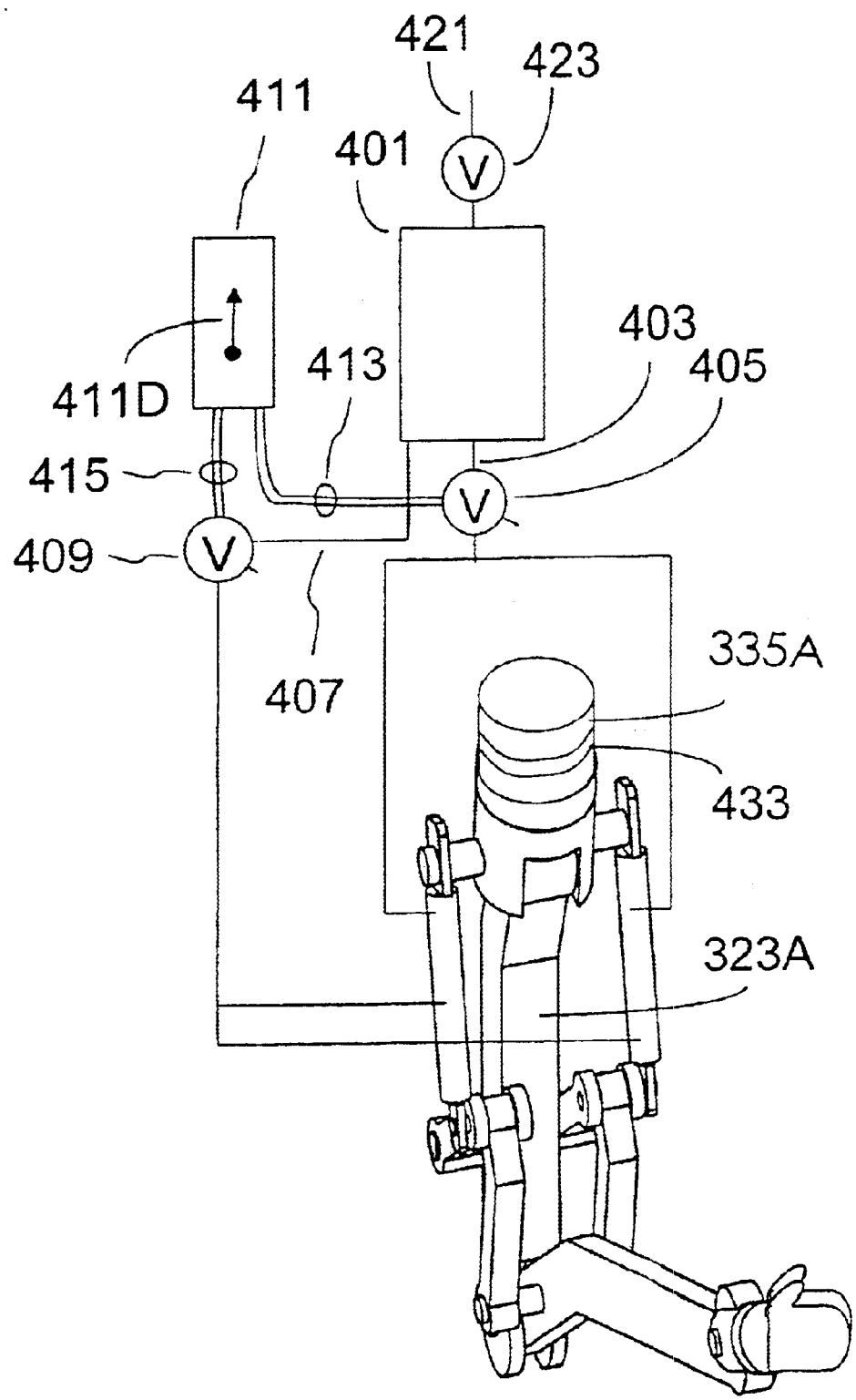
FIG. 33 is an isometric view of the prosthesis of FIG. 28 in the position of FIG. 32 and also showing a system for actuating the pistons of the cylinders coupled to the device.

Referring now to FIGS. 28–33, the prosthetic device 321A is the same as that of FIGS. 16–21, 26, and 27, except the member 323A is shorter than member 323 and the knob 323K is removed and the upper end 323U and cylinders 391 and 393 are pivotally coupled to the two plates 327A and 327B of member 331L by way of pin 395. The member 331 L is pivotally coupled to member 331U by a pin 333. Thus in FIGS. 28–33, members 331L and 331U are the same as members 331L and 331U of FIG. 22 except the exterior pin 351 and L shaped rods 347 are removed and the pin 395 is used in place of pin 329 to pivotally couple the upper end 323U and the two cylinders 391 and 393 to the two plates 327A and 327B of member 331L. The device 323A will be used to replace a lower arm where the upper arm has been amputated between the shoulder and the elbow. In FIGS. 28–33, like components are the same as those in FIGS. 16–21, 26, 27. The device 323A also comprises members 325, 352, 355, 356, which are the same as those of FIGS. 16–21, 26, and 27; links 371A, 373A, 371B, 373B which are the same as those of FIGS. 16–21, 26, and 27; cylinders 391, 393 and pistons 393P and 393P which are the same as those of FIGS. 16–21, 26, and 27; source 401, control unit 411, valves 405,409 which are the same as those of FIGS. 16–21, 26, and 27 all of which operate the same as the corresponding members of FIGS. 16–21, 26, and 27. In this respect by controlling unit 411 to control the cylinders-pistons 391, 391P and 393, 393P, the lower member 325 can be moved to the positions shown in FIGS. 28–33. The socket 335 and belt straps 337, 338, 137 will not be employed. Instead, a longer and larger diameter socket 335A will be used. It will be secured to the member 323A and the amputated upper arm will be inserted into the other end of the socket 335A and secured in place by straps 433 as shown in FIG. 33.

Figure 26:
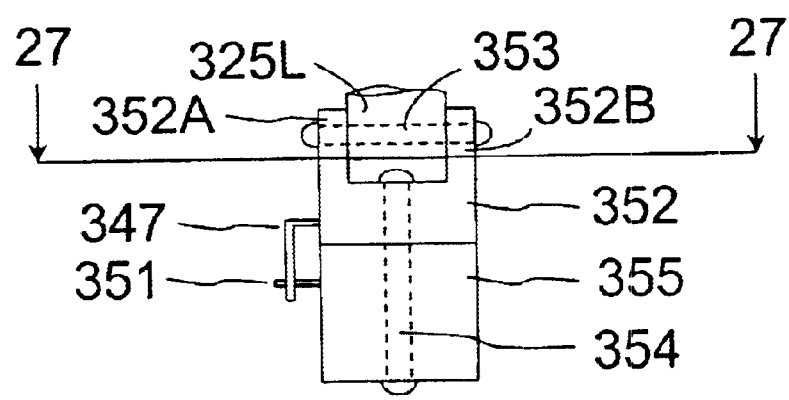
FIG. 26 is an apparatus for rotating the lower hand portion of the prosthesis of FIG. 16.
Figure 27:
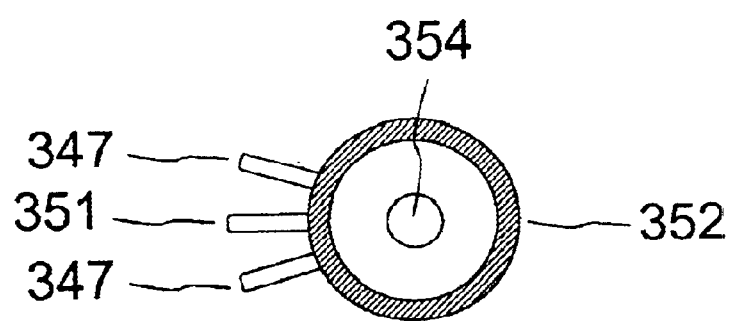
FIG. 27 is a view of FIG. 26 as seen along lines 27—27.
Figure 30:
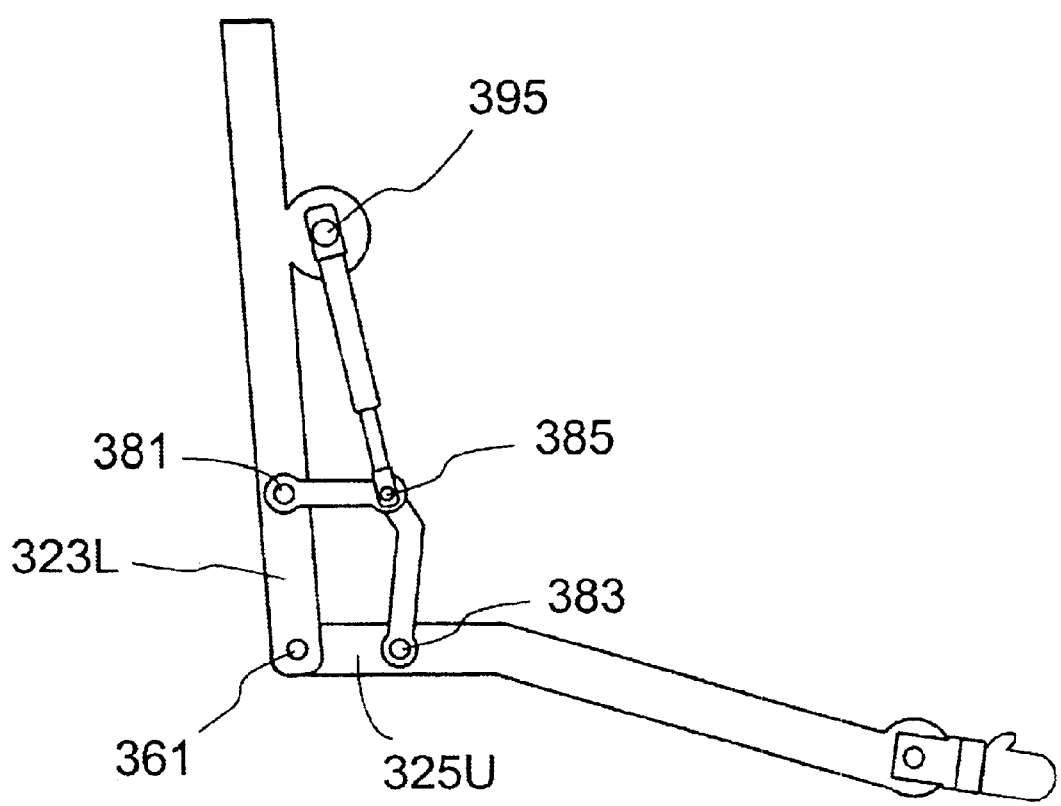
FIG. 30 is a side view of the prosthesis of FIG. 28 wherein the lower portion has been rotated about 90 degrees relative to the upper portion.
Figure 31:
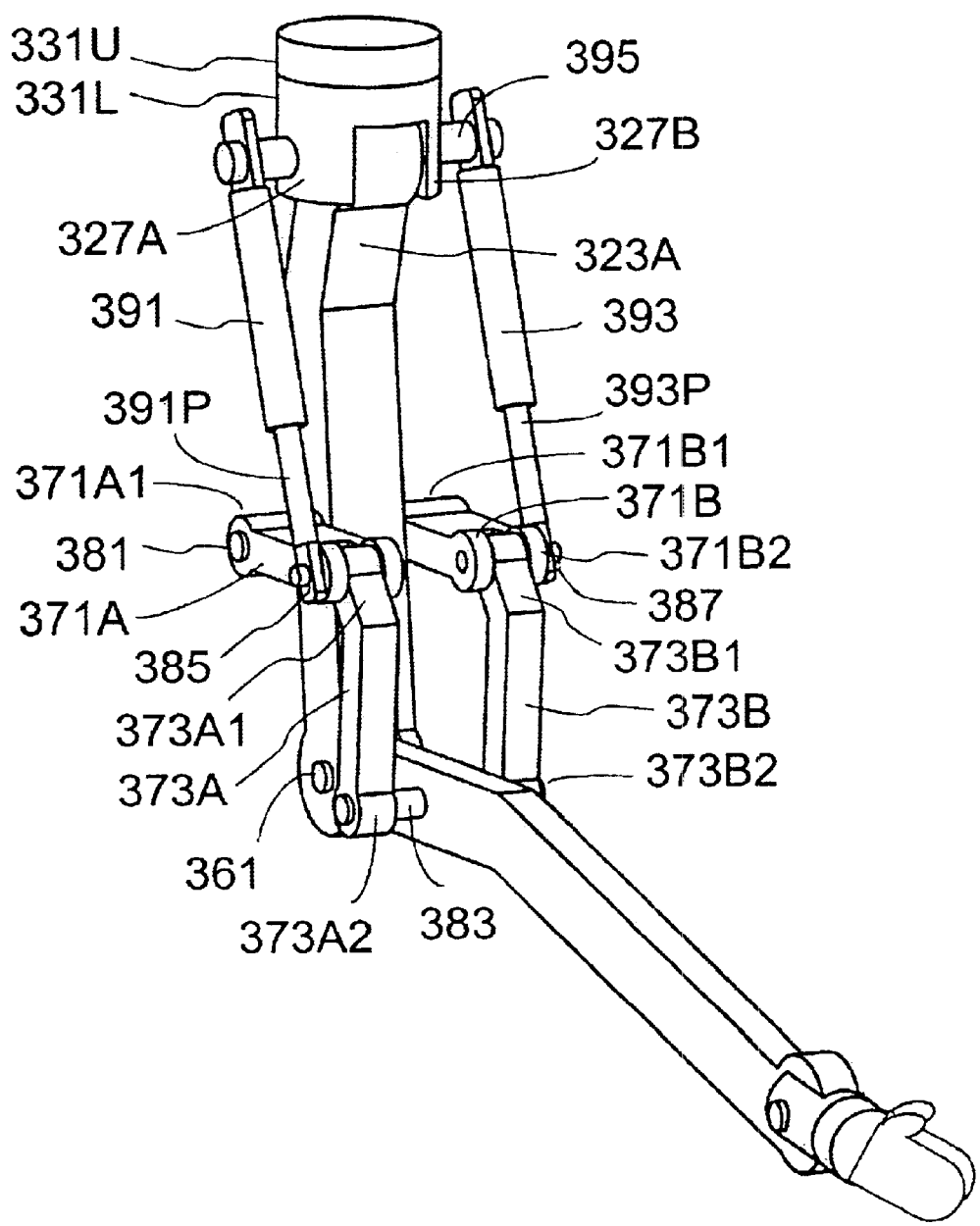
FIG. 31 is an isometric view of the prosthesis of FIG. 30.
Figure 32:
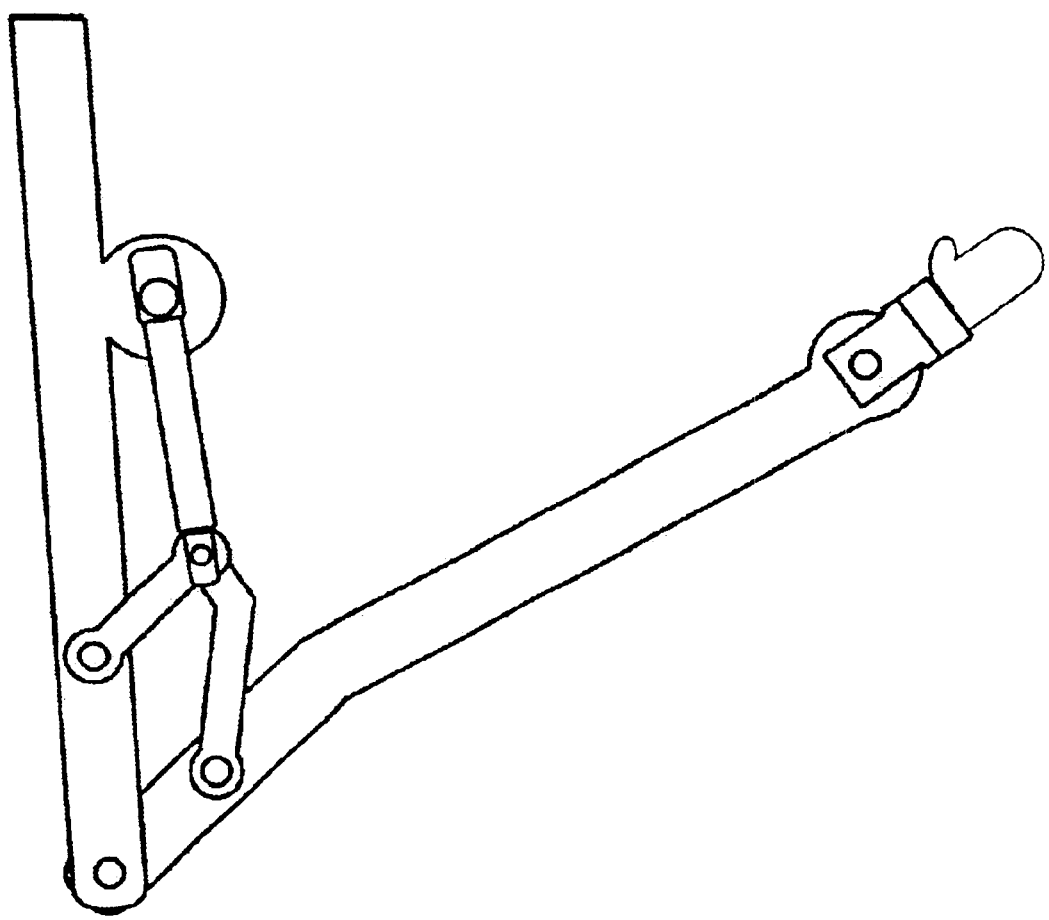
FIG. 32 is a side view of the prosthesis of FIG. 28 wherein the lower portion has been rotated to position to form an acute angle relative to the upper portion.

The members 352 and 355 will have the rotational limitation stops 347 and 351 as shown in FIGS. 26 and 27.

What is claimed:

1. A prosthesis for a limb of a person, comprising:

a first elongated member having first and second spaced apart ends, a second elongated member having first and second spaced apart ends, member coupling means for pivotally coupling said second end of said first member to said first end of said second member such that said first and second members may pivot relative to each other only about said member coupling means, at least one first link having first and second ends, coupling means for pivotally coupling said first end of said first link to said first member, at least one second link comprising a single member having first and second ends, coupling means for pivotally coupling said second end of said second link to said first end of said second member, link coupling means for pivotally coupling said second end of said first link to said first end of said second link, body coupling means for coupling said first end of said first member to a person, and power means for moving said first and second links to cause movement of said first and second members relative to each other.

2. The prosthesis of claim 1, wherein:

said second member can move between first and second positions relative to said first member, in said first position, said first and second members form an angle greater than 90 degrees relative to each other and in said second position, said first and second members form an acute angle relative to each other, said coupling means for pivotally coupling said second end of said second link to said first end of said second member and said link coupling means are located in a plane spaced from said first member when said second member is located in said first position, said power means can be actuated to move said second member to said first position and to said second position.

3. The prosthesis of claim 2, wherein:

said body coupling means comprises means for coupling said first member to a person in a position to allow said prosthesis to serve as a leg of a human.

4. The prosthesis of claim 3, wherein:

said power means comprises a fluid actuated cylinder and piston pivotally coupled to said first member and to said link coupling means.

5. The limb of claim 4, wherein:

said piston may be moved to a retracted position and to an extended position, when said piston is moved to an extended position, said second member is located in said second position, when said piston is moved to a retracted position, said second member is located in said first position.

6. The prosthesis of claim 4, comprising:

means for controlling the flow of fluid into and from said cylinder to move said piston to cause movement of said first and second links and hence movement of said second member relative to said first member.

7. The prosthesis of claim 1, wherein:

said first member and second member each comprises an edge portion, said second member can move in a first plane between a first position and a second position relative to said first member, in said first position, said edge portions of said first and second members face in the same direction, said link coupling means and said coupling means for pivotally coupling said second end of said second link to said first end of said second member are located in a second plane transverse to said first plane and spaced from said first member on said side of said edge portion of said first member when said second member is located in said first position.

8. A prosthesis for a limb of a person, comprising:

a first elongated member having first and second spaced apart ends, a second elongated member having first and second spaced apart ends, member coupling means for pivotally coupling said second end of said first member to said first end of said second member such that said first and second members may pivot relative to each other only about said member coupling means, at least one first link comprising a single member having first and second ends, coupling means for pivotally coupling said first end of said first link to said first member, at least one second link having first and second ends, coupling means for pivotally coupling said second end of said second link to said first end of said second member, link coupling means for pivotally coupling said second end of said first link to said first end of said second link, body coupling means for coupling said first end of said first member to a person to allow said prosthesis serve as a leg of a person, means for pivotally coupling said first end of said first member to said body coupling means for pivotal movement about a given axis, power means of moving said first and second links to cause movement of said second member such that said second member can pivot between first and second positions relative to said first member, in said first position, said first and second members form an angle relative to each other which is greater than 90 degrees and in said second position, said first and second members form an acute angle relative to each other.

9. The prosthesis of claim 8, wherein:

said power means comprises a fluid actuated cylinder and piston pivotally coupled to said first member at a position spaced from said first end of said first member and to said link coupling means, said piston may be moved to a retracted position and to an extended position, when said piston is moved to an extended position, said second member is located in said second position, when said position is moved to a retracted position, said second member is located in said first position.

10. The prosthesis of claim 9, wherein:

said body coupling means comprises a main coupling member to be coupled to a person and a rotatable member coupled to said main coupling member for rotation about an axis transverse to said given axis, said first end of said first member being pivotally coupled to said rotatable member.

11. A prosthesis for a limb of a person, comprising:

a first elongated member having first and second spaced apart ends, a second elongated member having first and second spaced apart ends, member coupling means for pivotally coupling said second end of said first member to said first end of said second member, at least one first link having first and second ends, coupling means for pivotally coupling said first end of said first link to said first member, at least one second link having first and second ends, coupling means for pivotally coupling said second end of said second link to said first end of said second member, link coupling means for pivotally coupling said second end of said first link to said first end of said second link, body coupling means for coupling said first end of said first member to a person, power means comprising a fluid actuated cylinder pivotally coupled to said first member and a piston pivotally coupled to said link coupling means, and means for controlling the flow of fluid into and from said cylinder to move said piston to cause movement of said first and second links and hence movement of said second member relative to said first member.

12. The prosthesis of claim 11, wherein:

said first and second members may pivot relative to each other only about said member coupling means, said second link comprises a single member.

13. A prosthesis for a limb of a person, comprising:

first and second elongated members, each having opposite ends, member coupling means for pivotally coupling said first and second members together such that said first and second members may pivot relative to each other only about said member coupling means, at least one first link, coupling means for pivotally coupling said first link to said first member, at least one second link comprising a single member, coupling means for pivotally coupling said second link to said second member, link coupling means for pivotally coupling said first and second links together, body coupling means for coupling an end of said first member to a person, and power means for moving said first and second links to cause movement of said first and second members relative to each other, said power means comprises a fluid actuated cylinder and a piston pivotally coupled to said first member and to said link coupling means.

14. The prosthesis of claim 13, comprising:

means for controlling the flow of fluid into and from said cylinder to move said piston to cause movement of said first and second links and hence movement of said second member relative to said first member.

15. A prosthesis for a limb of a person, comprising:

first and second elongated members, each having opposite ends, member coupling means for pivotally coupling said first and second members together such that said first and second members may pivot relative to each other only about said member coupling means, at least one first link, coupling means for pivotally coupling said first link to said first member, at least one second link comprising a single member, coupling means for pivotally coupling said second link to said second member, link coupling means for pivotally coupling said first and second links together, body coupling means for coupling an end of said first member to a person, power means for moving said first and second links to cause movement of said first and second members relative to each other, said power means comprises a fluid actuated cylinder and a piston pivotally coupled to said first member and to said link coupling means.

16. The prosthesis of claim 15, comprising:

means for controlling the flow of fluid into and from said cylinder to move said piston to cause movement of said first and second links and hence movement of said second member relative to said first member.

17. The prosthesis of claim 15, wherein:

said first member and second member each comprises an edge portion, said second member can move in a first plane between a first position and a second position relative to said first member, in said first position, said edge portions of said first and second members face in the same direction, said link coupling means and said means for pivotally coupling said second link to said second member are located in a second plane transverse to said first plane and spaced from said edge portion of said first member when said second member is located in said first position.

18. A prosthesis for a limb of a person comprising:

first and second elongated members, each having opposite ends, member coupling means for pivotally coupling said first and second members together, such that said first and second members may pivot relative to each other only about said member coupling means, a pair of first links, means for pivotally coupling said pair of first links to said first member on opposite sides, thereof, a pair of second links, means for pivotally coupling said pair of second links to said second member on opposite sides thereof, link coupling means for pivotally coupling together said first and second links of one pair and said first and second links of the other of said pairs, body coupling means for coupling an end of said first member to a person, power means for moving each of said pairs of said first and second links to cause movement of said first and second members relative to each other.

19. The prosthesis of claim 18, wherein:

said first member and second member each comprises an edge portion, said second member can move in a first plane between a first position and a second position relative to said first member, in said first position, said edge portion of said first and second members face in the same direction, said link coupling means and said means for pivotally coupling said pair of second links to said second member are located in a second plane transverse to said first plane and spaced from said first member on said side of said edge portion of said first member when said second member is located in said first position.

20. The prosthesis of claim 19, wherein:

each of said second links comprises a single member.

21. The prosthesis of claim 18, wherein:

each of said second links comprises a single member.

22. The prosthesis of claim 18, wherein:

each of said second links of said pair of second links has two portions which define an obtuse angle with the apex thereof facing in said first direction when said second member is in said first position.

* * * * *